United States Patent
Dunham et al.

(10) Patent No.: US 8,747,783 B2
(45) Date of Patent: Jun. 10, 2014

(54) ACID ALKYLATION SYSTEM AND PROCESS FOR CONTROLLING TEMPERATURE IN A SETTLER

(75) Inventors: Daryl Dunham, Ponca City, OK (US); Dale James Shields, Grayslake, IL (US)

(73) Assignee: UOP LLC, Des Plaines, IL (US)

( * ) Notice: Subject to any disclaimer, the term of this patent is extended or adjusted under 35 U.S.C. 154(b) by 1386 days.

(21) Appl. No.: 12/490,678

(22) Filed: Jun. 24, 2009

(65) Prior Publication Data

US 2010/0331598 A1    Dec. 30, 2010

(51) Int. Cl.
  *B01J 19/00* (2006.01)
  *C07C 2/62* (2006.01)
  *C07C 2/58* (2006.01)
  *C07C 2/00* (2006.01)
  *B01J 8/00* (2006.01)
  *B01J 8/04* (2006.01)

(52) U.S. Cl.
  USPC ........... 422/630; 422/649; 422/198; 422/129; 422/187; 585/709

(58) Field of Classification Search
  USPC ......... 422/608, 618, 630, 649, 198, 234, 129, 422/187; 585/709, 331
  See application file for complete search history.

(56) References Cited

U.S. PATENT DOCUMENTS

| | | | |
|---|---|---|---|
| 2,287,931 A * | 6/1942 | Corson et al. | 208/64 |
| 2,615,928 A | 10/1952 | Jolly | |
| 3,914,110 A * | 10/1975 | Anderson | 422/200 |
| 3,914,111 A * | 10/1975 | Anderson | 422/200 |
| 4,046,516 A | 9/1977 | Burton et al. | |
| 4,677,244 A * | 6/1987 | Hachmuth et al. | 585/701 |
| 4,783,567 A | 11/1988 | Kocal | |
| 4,863,697 A | 9/1989 | Hann et al. | |
| 5,098,668 A | 3/1992 | Callen et al. | |
| 5,114,675 A | 5/1992 | Greco et al. | |
| 5,185,469 A | 2/1993 | Lindley et al. | |
| 5,209,907 A | 5/1993 | Hovis | |
| 5,258,568 A | 11/1993 | Child et al. | |
| 5,407,830 A | 4/1995 | Altman et al. | |
| 5,583,049 A | 12/1996 | Altman et al. | |
| 5,789,640 A | 8/1998 | Jin et al. | |
| 6,106,789 A * | 8/2000 | Thompson et al. | 422/201 |
| 6,172,274 B1 | 1/2001 | Gosling | |
| 6,187,986 B1 | 2/2001 | Schlaeppi | |
| 2003/0158457 A1* | 8/2003 | Gershuni | 585/719 |

OTHER PUBLICATIONS

Hewson, HF Alkylation, The Oil and Gas Journal, Mar. 22, 1954, vol. 52, No. 46, pp. 189, 192-193, 195, 202.
Shanley et al., Numerous Improvements in HF Alkylation Will Cut Costs and Reduce Losses, The Oil and Gas Journal, Dec. 1, 1945, vol. 44, No. 30, pp. 94-96, 98.
Stewart et al., Design Concepts for a Hydrogen Fluoride Emergency De-Inventory System, Process Safety Progress, Apr. 1994, vol. 13, No. 2, pp. 105-107.
Thornton, Jr., Three Unusual Features in New HF Alkylation Unit, Petroleum Processing, Oct. 1954, vol. 9, No. 10, pp. 1570-1573.

* cited by examiner

*Primary Examiner* — Natasha Young
(74) *Attorney, Agent, or Firm* — James C Paschall

(57) ABSTRACT

One exemplary embodiment can be an acid alkylation system. The system can include a cooler-reactor and a settler. The settler can have a height and a width. Usually, the height exceeds the width. Generally, the cooler-reactor receives a feed of at least one of a stream including an olefin and a stream including an isobutane. Typically, at least a portion of one of the streams is bypassed around the cooler-reactor to the settler to control the temperature within the settler.

17 Claims, 1 Drawing Sheet

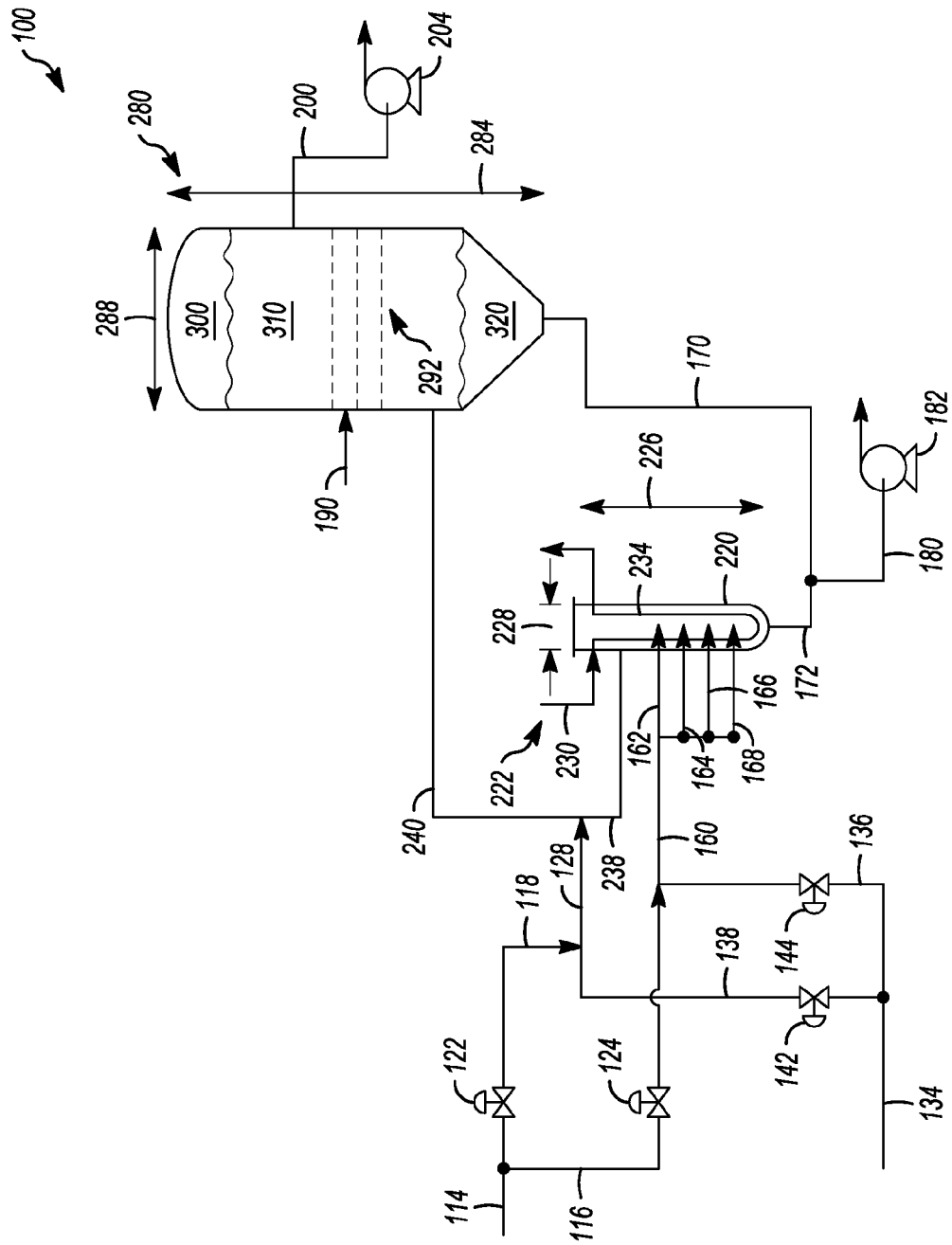

ACID ALKYLATION SYSTEM AND PROCESS FOR CONTROLLING TEMPERATURE IN A SETTLER

FIELD OF THE INVENTION

This invention generally relates to an acid alkylation system, and at least one process relating thereto.

DESCRIPTION OF THE RELATED ART

Generally, alkylation is a process that can be used to produce a high quality, high octane gasoline from lower boiling feeds. Usually, commercial refinery plants alkylate a feed including an isoparaffin stream, typically including isobutane, and an olefin stream, typically including one or more C3-C4 olefins, to form branch chain paraffin products boiling in the gasoline range, which can include hydrocarbons boiling up to about 200° C.

One such process can include a settler providing an alkylation catalyst via gravity to an alkylation reactor. An advantage of such processes can be providing a lower pressure in the system. However, such processes can have a greater inventory of alkylation catalyst as compared to other processes, such as those processes using a pump to transfer the alkylation catalyst from the settler to the alkylation reactor.

As a consequence, it is generally preferable to operate an alkylation system at the lowest pressure and alkylation catalyst inventory as possible. Consequently, it would be beneficial to provide an alkylation system with a gravity-fed alkylation catalyst and a low catalyst inventory.

Also, often a pump is used to transfer one or more hydrocarbons to one or more downstream fractionation columns. It would be beneficial to control the temperature in the settler to improve the operability of the pump transferring the hydrocarbon from the settler vessel to the columns.

SUMMARY OF THE INVENTION

One exemplary embodiment can be an acid alkylation system. The system can include a cooler-reactor and a settler. The settler can have a height and a width. Usually, the height exceeds the width. Generally, the cooler-reactor receives a feed of at least one of a stream including an olefin and a stream including an isobutane. Typically, at least a portion of one of the streams is bypassed around the cooler-reactor to the settler to control the temperature within the settler.

Another exemplary embodiment can be an acid alkylation system. Typically, the acid alkylation system includes a cooler-reactor and a settler. The settler can have a height and a width. Usually, the height exceeds the width. The cooler-reactor can receive a feed including one or more olefins and one or more isoparaffins. Typically, at least a portion of the one or more isoparaffins is bypassed around the cooler-reactor and provided to the settler to control the temperature within the settler.

A further exemplary embodiment can be a process for controlling the temperature in a settler downstream from an alkylation reactor. The process can include bypassing at least one of a stream rich in one or more olefins and a stream rich in one or more isoparaffins around the alkylation reactor to the settler for controlling the temperature in the settler.

In the embodiments provided herein, the acid:hydrocarbon ratio can be lower than a typical acid gravity-fed system. Lowering the acid inventory can reduce the risk to personnel operating the systems. Moreover, the benefits of the gravity-fed system can still be obtained, such as operating at a lower pressure. In addition, the bypassing of the feeds around the reactor can control the temperature, and hence the vapor pressure of hydrocarbons within the settler. Thus, operability of the hydrocarbon phase transfer pump can be controlled with a relatively high degree of reliability. What is more, an existing gravity-fed alkylation riser-reactor can be modified with a cooler-reactor by, e.g., replacing a cooling water exchanger with the cooler-reactor. Generally, cooling a feed with a cooling water exchanger requires a greater inventory of material to absorb the heat of reaction as compared to cooling the reactants and products during the reaction with a cooler-reactor. Thus, the acid inventory may be lowered.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Additionally, characterizing a stream as, e.g., an "olefin stream" or a "water stream" can mean a stream including or rich in, respectively, at least one olefin or water.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "bypass" can mean providing a stream to a vessel without recycling from, e.g., downstream fractionation. Typically, a stream is bypassed around a cooler-reactor and may pass through a line or another reactor, such as a riser-reactor, before entering a settler.

As used herein, the term "rich" can mean an amount of at least generally about 30%, preferably about 50%, and optimally about 70%, by mole, of a compound or class of compounds in a feed, an effluent, a stream, or a portion.

As used herein, the term "substantially" can mean an amount of at least generally about 80%, preferably about 90%, and optimally about 99%, by mole, of a compound or class of compounds in a feed, an effluent, a stream, or a portion.

As used herein, the term "vapor" can mean a gas or a dispersion that may include or consist of one or more hydrocarbons.

As used herein, the term "vaporization" can mean using at least one of heat and pressure to change at least a portion of a liquid to a gas optionally forming a dispersion, such as a gas entraining at least one of liquid and solid particles.

As used herein, the term "hydrogen fluoride" can include at least one of a hydrogen fluoride or a hydrofluoric acid. Generally, a hydrofluoric acid is a solution of a hydrogen fluoride in water, where the hydrogen fluoride can disassociate and may form ions of $H_3O^+$, $H^+$, $FHF^-$, and $F^-$.

As depicted, process flow lines in the figures can be referred to as lines, pipes, spargers, feeds, effluents, streams, or portions. Particularly, a line, a sparger, or a pipe can contain one or more feeds, effluents, streams or portions, and one or more feeds, effluents, streams, or portions can be contained by a line, a sparger, or a pipe. Generally, a sparger is a pipe forming a plurality of holes to improve dispersing of material from inside the pipe.

BRIEF DESCRIPTION OF THE DRAWING

FIG. 1 is a schematic depiction of an exemplary acid alkylation unit or system.

DETAILED DESCRIPTION

Referring to FIG. 1, an acid alkylation unit or system 100 can include an alkylation reactor 220, such as a cooler-reactor, and a settler 280. Although a cooler-reactor is depicted, it should be understood that other reactors may be utilized. Other equipment that may be utilized, such as an acid regeneration tower and one or more distillation columns, are not depicted. Some of the features and/or contents of at least one vessel are depicted schematically in a cross-sectional view.

The cooler-reactor 220 can have an end 222 as well as a height 226 and a width 228. Generally, the height 226 exceeds the width 228. At the end 222, a cooling water stream 230 can be provided. The cooling water stream 230 can enter one or more cooling coils 234 to remove the heat generated by the reactants in the cooler-reactor 220. Usually, the reaction can be carried out at pressures varying from about 100-about 7,000 kPa, preferably about 800-about 1,600 kPa, with a residence time of about 20-about 300 seconds. The temperature of the reaction can vary but usually ranges from about −40-about 70° C. In the reaction of, e.g., an isoparaffin, such as isobutane with a C3 and/or a C4 olefin, the reaction temperature is preferably about 15-about 40° C.

The settler 280 can have a height 284 and a width 288, with the height 284 exceeding the width 288. Usually, the width 288 can be the diameter of the settler 280. The settler 280 can include one or more contacting trays 292 for removing fluorides, which can reduce downstream equipment for removing such radicals. Generally, the settler can recycle the acid catalyst via gravity, as hereinafter described. The settler 280 can operate at a pressure of up to about 1,100 kPa, preferably about 800-about 1,100 kPa.

The acid alkylation unit or system 100 can receive a stream including or rich in an olefin 114 and a stream including or rich in an isoparaffin 134. Typically, the isoparaffin is isobutane. Usually, the alkylation reaction can include the reaction of an isoparaffin, such as isobutane, with an olefin or other alkylating agent such as propylene, isobutylene, butene-1, butenes-2, and amylenes. Generally, the reaction of an isoparaffin with a C3 or a C4 olefin, such as isobutylene, butene-1, and/or butenes-2, is an example of a preferred reaction involving these specified materials and mixture. One preferred mixture is an isoparaffin and typically a mixed "butene" produced from a catalytic cracking operation, which can include about 25%, by volume, of butene-1, about 30%, by volume, of isobutylene, and about 45%, by volume, of butenes-2. Typically, the stream rich in isobutane can at least be partially provided by recycling isobutane from a downstream fractionation zone, and includes make-up isobutane from a refinery or a chemical manufacturing unit.

Typically, the alkylation catalyst can include hydrogen fluoride, a sulfuric acid, a hydrofluoric acid, a phosphoric acid, a metal halide, or other suitable alkylation catalyst. Preferably, the catalyst is a hydrofluoric acid. Generally, the alkylation reaction is carried out with substantial molar excess of isoparaffin to olefin, typically in excess of about 1:1, usually about 4:1-about 70:1, preferably about 5:1-about 20:1. Usually, the system or unit 100 can maintain an acid:hydrocarbon volume ratio of less than about 3:1, preferably less than about 2.5:1. As a consequence, the embodiments disclosed herein can obtain the benefits of a gravity-fed settler system with reduced acid inventories. Generally, the volume ratio of acid:hydrocarbon can be about 1:1-about 3.0:1. This volume can be less than what is required for typical gravity-driven units with riser-reactors that can operate with an acid:hydrocarbon ratio of about 4:1. The gravity-driven system can operate at a lower pressure reducing the risk of leaks due to increased pressures. Thus, the catalyst inventory can be reduced without adding a pump for acid circulation. Moreover, employing a heat exchanger in the reaction zone can reduce the amount of catalyst circulation normally required as a heat sink in a gravity-driven riser-reactor system.

The stream rich in olefin 114 can have at least a portion 118 bypassing the cooler-reactor 220. The at least a portion 118 can be up to about 40%, about 1-about 40%, and optimally about 10-about 40%, by volume, of the stream rich in olefin 114. Similarly, at least a portion 138 of the stream 134 can be bypassed around the cooler-reactor 220. The at least a portion 138 can be up to about 30%, preferably about 1-about 30%, and optimally about 5-about 30%, by volume, of the stream 134. A first valve 122 and a second valve 124, preferably control valves, can control the amount of the stream 114 rich in olefin bypassed around the cooler-reactor 220. Similarly, a first valve 142 and a second valve 144, preferably control valves, can control the amount of the stream 134 rich in isoparaffins that is bypassed around the cooler-reactor 220. Bypassing the streams 118 and 138 around the cooler-reactor 220 can control the temperature, and hence, the pressure in the settler 280. Generally, the bypassing is controlled by measuring the pressure within the settler 280. Typically, a minimum pressure is desired in the vessel to maintain the reliability of a fluid transfer device 204, typically a pump.

A stream 116 rich in olefin that remains after the bypass portion 118 is removed can be combined with the stream 136 rich in isoparaffin that remains after bypass portion 138 is removed. These streams 116 and 136 can be combined as a feed 160 for the cooler-reactor 220. The feed 160 can be split through several spargers, namely a sparger 162, a sparger 164, a sparger 166, and a sparger 168 before entering the cooler-reactor 220. Thus, the vertically spaced spargers 162, 164, 166, and 168 can ensure good dispersion of the hydrocarbons through the acid phase in the cooler-reactor 220. This rigorous mixing of the hydrocarbon and acid catalyst can minimize the amount of acid in the unit 100. Generally, the acid catalyst can enter the cooler-reactor 220 via a line 172, as hereinafter described. The reaction temperature can be cooled by the cooling water 230 in the one or more cooling coils 234, which generally removes the heat of the reaction. Afterwards, the reaction products or reaction effluent can exit the cooler-reactor 220 through a line 238. Afterwards, the bypassed olefin and isobutane portions 118 and 138 can be combined as a combined bypass stream 128. This stream 128 can enter the line 238 and be provided to the settler via a line 240.

Alternatively, the lines 238 and 240 can collectively form a riser-reactor, which may have vertical and horizontal sections optionally with the same diameter. The combined bypass stream 128 can act as a feed and optionally be provided through one or more spargers. The alkylation reaction can continue to an inlet of the settler 280 and occur at a pressure of about 100-about 7,000 kPa, preferably about 400-about 1,600 kPa with a residence time of about 10-about 300 seconds. The temperature of the reaction can vary but usually ranges from about −40-about 70° C. In the reaction of, e.g., an isoparaffin, such as isobutane with a C3 and/or a C4 olefin, the reaction temperature is preferably about 15-about 40° C. In this exemplary embodiment, the heat of the reaction may not be removed from the riser-reactor.

The settler 280 can receive the reaction effluent, which can separate into a vapor phase 300, a hydrocarbon phase 310, and an alkylation catalyst or an acid phase 320. Thus, the temperature, and hence the pressure, in the settler can be controlled by bypassing amounts of the olefin and/or isobutane reactants to prevent an overpressure within the settler 280 and provide proper suction for the fluid transfer device 204, typically a pump. The hydrocarbon phase 310, including one or more hydrocarbons, can exit via a line 200 to the fluid transfer device 204. The hydrocarbons can be pumped to downstream fractionation where an alkylate product can be separated as well as an isoparaffin, such as isobutane, which can be recycled. The acid catalyst phase 320 can be withdrawn from the bottom of the settler 280 via the line 170. A portion can be withdrawn through a line 180 and transferred by a fluid transfer device 182, typically a pump, to a catalyst regeneration zone, which can typically include one or more acid regeneration towers. The regenerated acid catalyst can be returned via a line 190 to the settler 280, although the regenerated catalyst can be provided to other locations within the system 100, such as the combined feed stream 160.

Any suitable control scheme may be utilized for, e.g., bypassing a portion of the streams 114 and 134 around the cooler-reactor 220. One or more exemplary settlers, alkylation reactors, fractionation zones, and catalyst regeneration zones, are disclosed in, e.g., U.S. Pat. No. 5,098,668. The embodiments disclosed herein can be used in a new alkylation unit or modify an existing alkylation unit.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An acid alkylation system, comprising:
    A) a cooler-reactor;
    B) a settler having a height and a width wherein the height exceeds the width wherein the cooler-reactor receives a feed of at least one of a stream comprising an olefin and a stream comprising an isobutane wherein at least a portion of one of the streams is bypassed around the cooler-reactor to the settler to control the temperature within the settler; and
    C) a riser-reactor in downstream communication with an olefin bypass line and an isobutane bypass line for receiving at least the portion of the at least one of the stream bypassed around the cooler-reactor before entering the settler, the olefin bypass line is out of downstream communication with the isobutane stream and the isobutane bypass line is out of downstream communication with the olefin stream.

2. The acid alkylation system according to claim 1, wherein at least a portion of the olefin stream is bypassed around the cooler-reactor.

3. The acid alkylation system according to claim 2, wherein up to about 40%, by volume, of the olefin stream is bypassed around the cooler-reactor.

4. The acid alkylation system according to claim 2, wherein about 10-about 40%, by volume, of the olefin stream is bypassed around the cooler-reactor.

5. The acid alkylation system according to claim 1, wherein at least a portion of the isobutane stream is bypassed around the cooler-reactor.

6. The acid alkylation system according to claim 5, wherein up to about 30%, by volume, of the isobutane stream is bypassed around the cooler-reactor.

7. The acid alkylation system according to claim 5, wherein about 5-about 30%, by volume, of the isobutane stream is bypassed around the cooler-reactor.

8. The acid alkylation system according to claim 1, wherein the cooler-reactor receives an alkylation catalyst in a volume ratio of alkylation catalyst:feed of about 1:1-about 3.0:1.

9. The acid alkylation system according to claim 1, wherein at least a portion of the olefin stream and the isobutane stream are combined before entering the cooler-reactor.

10. The acid alkylation system according to claim 9, wherein the isobutane:olefin mole ratio is about 1:1-about 20:1.

11. The acid alkylation system according to claim 10, wherein the combined feed is split before entering the cooler-reactor.

12. The acid alkylation system according to claim 11, wherein the cooler-reactor has a height and a width wherein the height exceeds the width and one end of the cooler-reactor is adapted to receive a cooling water stream.

13. The acid alkylation system according to claim 12, wherein the cooler-reactor comprises one or more cooling coils adapted to receive the cooling water stream.

14. An acid alkylation system, comprising:
    A) a cooler-reactor in communication with a stream rich in one or more olefins and a stream rich in one or more isoparaffins wherein at least a portion of the stream rich in one or more isoparaffins and at least a portion of the stream rich in one or more olefins is bypassed around the cooler-reactor;
    B) an olefin bypass line in communication with the stream rich in one or more olefins and out of downstream communication with the stream rich in one or more paraffins;
    C) an isoparaffin bypass line in communication with the stream rich in at least one or more isoparaffins and out of downstream communication with the stream rich in one or more olefins; and
    D) a settler in downstream communication with the olefin bypass line and the isoparaffin bypass line, the settler having a height and a width wherein the height exceeds the width.

15. The acid alkylation system according to claim 14, wherein the one or more isoparaffins comprises isobutane.

16. The acid alkylation system according to claim 14, wherein the one or more olefins comprises at least one of a C3 and a C4 olefin.

17. The acid alkylation system according to claim 14, wherein up to about 40%, by volume, of the one or more olefins is bypassed around the cooler-reactor.

\* \* \* \* \*